United States Patent
Sung et al.

(10) Patent No.: US 8,254,525 B2
(45) Date of Patent: Aug. 28, 2012

(54) X-RAY SCANNING SYSTEM PERFORMING SYNCHRONIZATION USING WIRELESS SIGNAL

(75) Inventors: Ki-Bong Sung, Gyeonggi-do (KR); Jong-Lae Park, Seoul (KR)

(73) Assignee: Poskam Co., Ltd., Gyeonggi-do (KR)

( * ) Notice: Subject to any disclaimer, the term of this patent is extended or adjusted under 35 U.S.C. 154(b) by 130 days.

(21) Appl. No.: 12/527,081

(22) PCT Filed: Mar. 25, 2008

(86) PCT No.: PCT/KR2008/001660
§ 371 (c)(1),
(2), (4) Date: Feb. 20, 2010

(87) PCT Pub. No.: WO2008/120886
PCT Pub. Date: Oct. 9, 2008

(65) Prior Publication Data
US 2010/0166143 A1    Jul. 1, 2010

(30) Foreign Application Priority Data

Mar. 30, 2007 (KR) ........................ 10-2007-0031448

(51) Int. Cl.
*H05G 1/56* (2006.01)

(52) U.S. Cl. ...................................................... 378/114
(58) Field of Classification Search ................... 378/62, 378/98.8, 114–116
See application file for complete search history.

(56) References Cited

U.S. PATENT DOCUMENTS

2006/0008054 A1 *    1/2006   Ohara ........................... 378/114

FOREIGN PATENT DOCUMENTS

| JP | 11-151233 A | 6/1999 |
| JP | 2003047607 A | 2/2003 |

OTHER PUBLICATIONS

PCT/KR2008/001660 International Search Report.

* cited by examiner

*Primary Examiner* — Courtney Thomas
(74) *Attorney, Agent, or Firm* — Lowe, Hauptman, Ham & Berner, LLP

(57) ABSTRACT

The present invention relates to an X-ray scanning system which is used to synchronize the preheating of an X-ray irradiation unit and the initialization of a digital image panel using wireless synchronization signals. The preheating of the X-ray irradiation unit and the initialization of the digital image panel are synchronized with each other using the wireless synchronization signal generated by the user's commands inputted through a hand-held switch unit. This makes it possible to conveniently take an X-ray image of an object.

4 Claims, 5 Drawing Sheets

[Fig. 1]
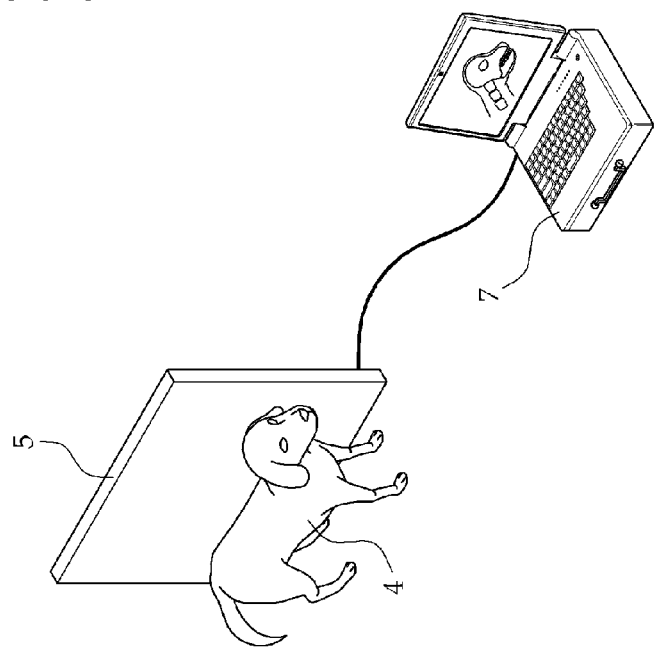
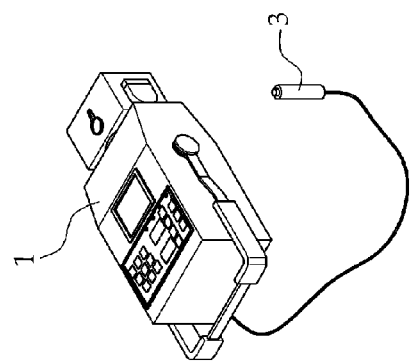

[Fig. 2]
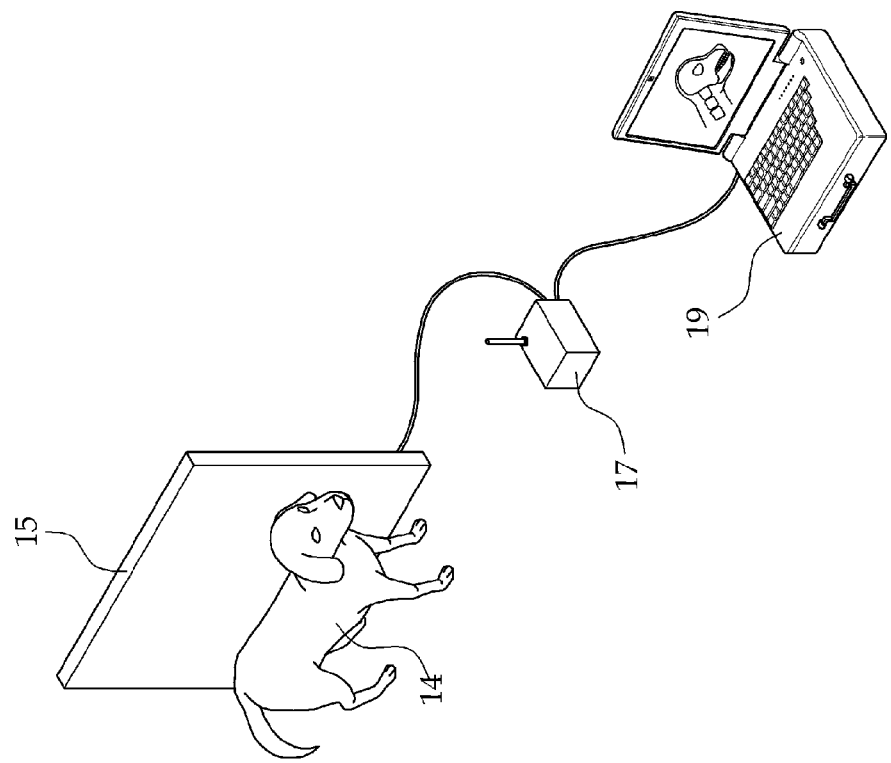
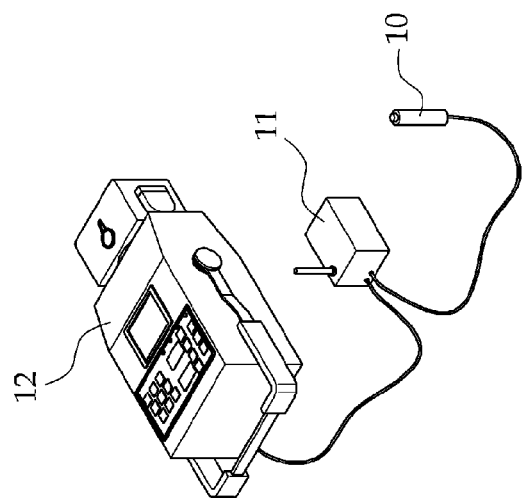

[Fig. 3]
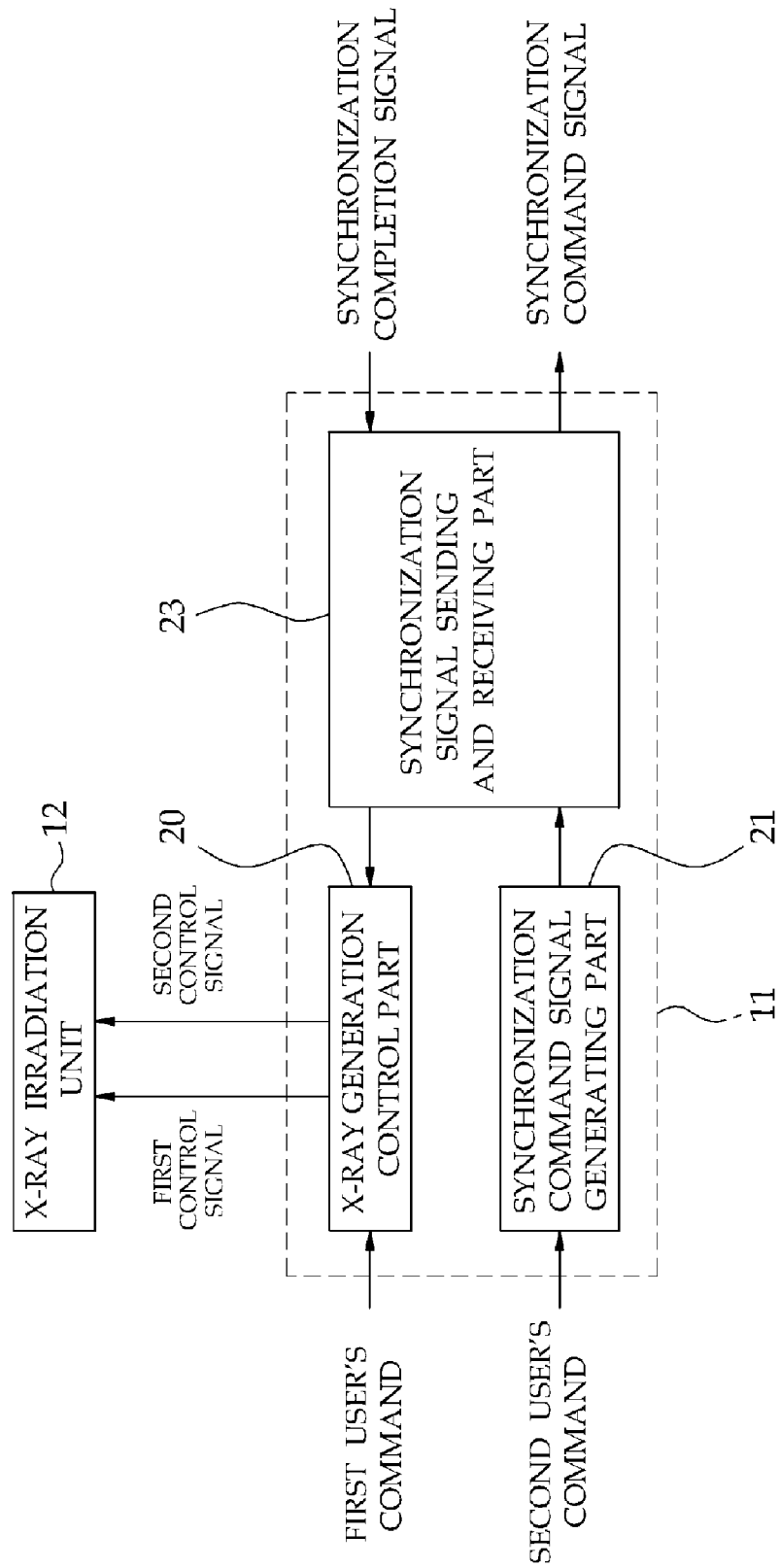

[Fig. 4]
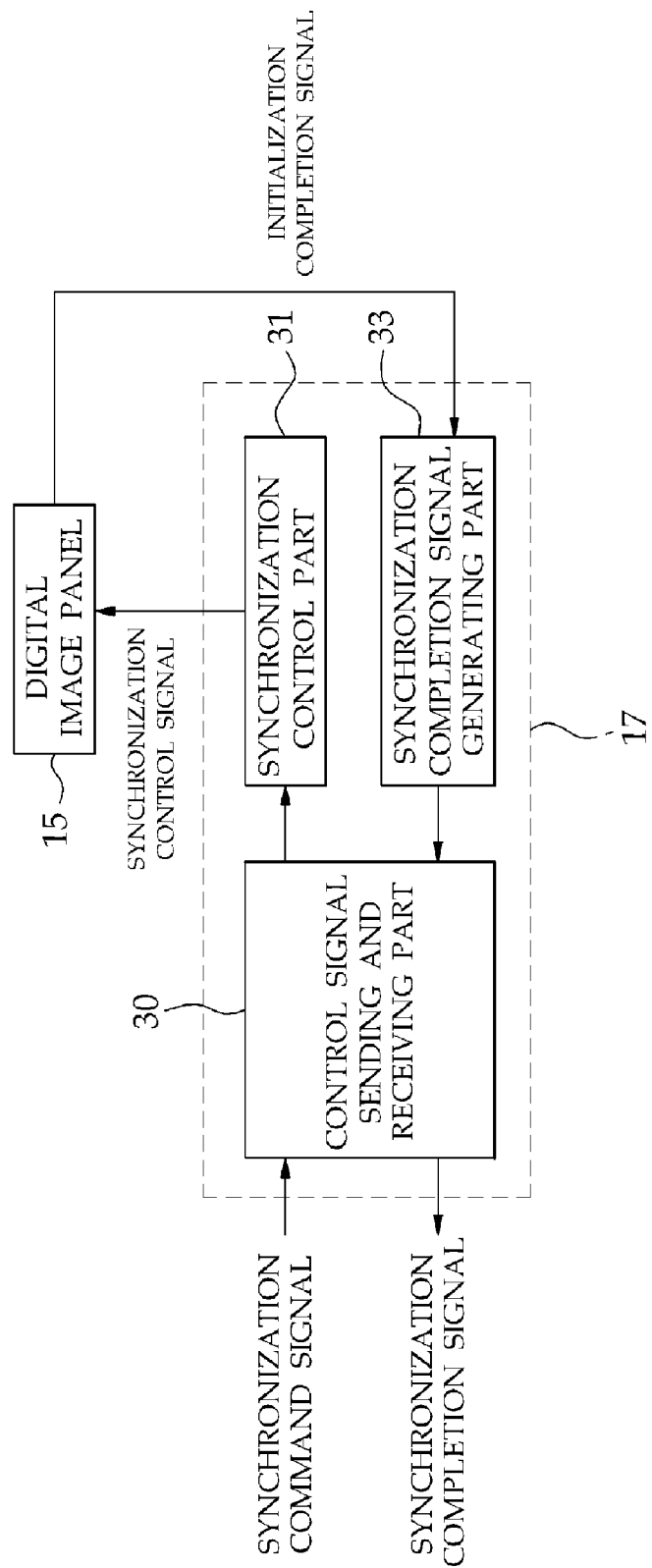

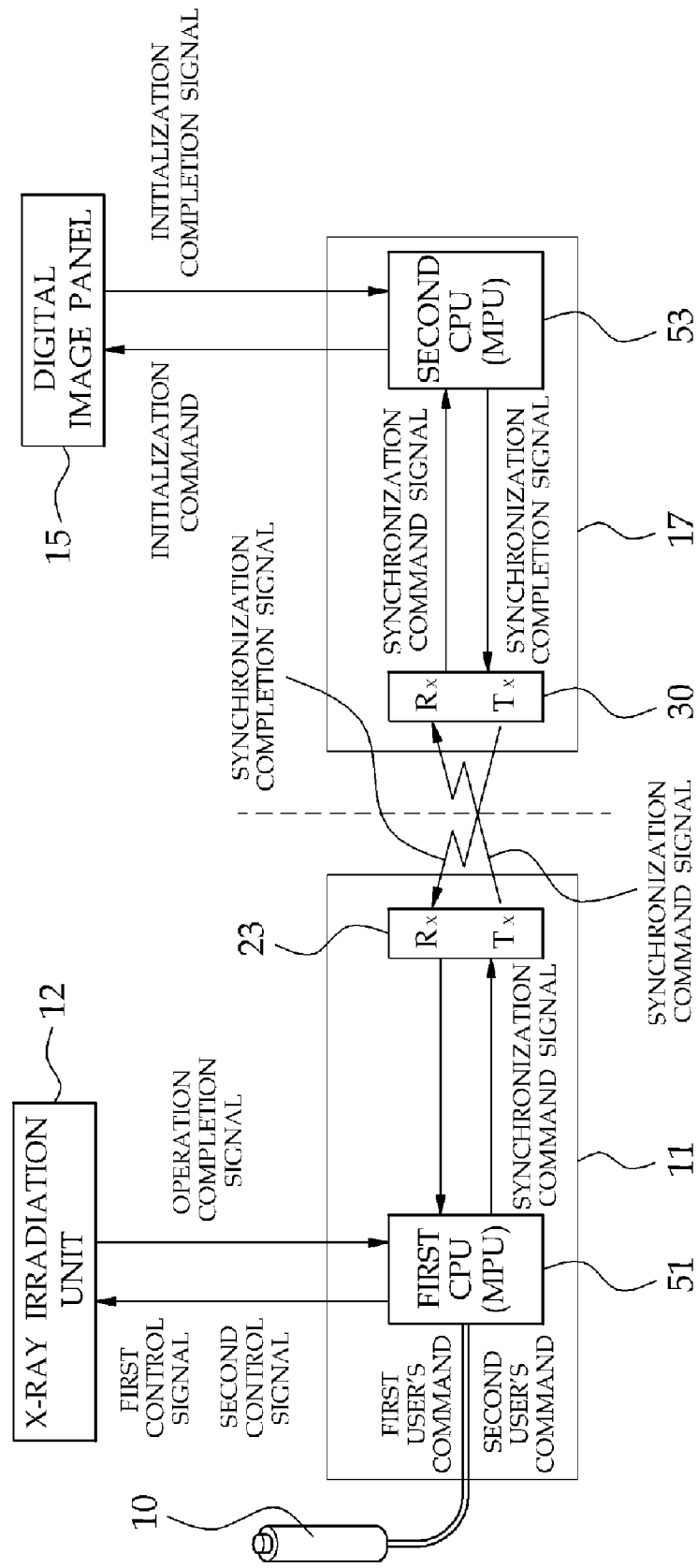
[Fig. 5]

X-RAY SCANNING SYSTEM PERFORMING SYNCHRONIZATION USING WIRELESS SIGNAL

RELATED APPLICATIONS

The present application is based on, International Application PCT/KR2008/001660, filed Mar. 25, 2008 and claims priority from, Korea Application Number 10-2007-0031448, filed Mar. 30, 2007, the disclosures of which are hereby incorporated by reference herein in their entirety.

TECHNICAL FIELD

The present invention relates to an X-ray scanning system. More particularly, the present invention relates to an X-ray scanning system for performing synchronization between an X-ray irradiation unit and an X-ray digital image panel using a wireless synchronization signal.

BACKGROUND ART

An X-ray scanning system refers to a device that inspects and diagnoses the internal status of a hidden object by transmitting X-rays through an object such as a human patient, an animal, a sealed package or the like and acquiring an image from the X-rays coming out of the object. A conventional X-ray scanning system includes an X-ray irradiation unit for generating X-rays and irradiating the X-rays on an object and an image acquiring part for sensing the X-rays transmitted through the object and acquiring an X-ray image of the object. Typically, an X-ray (sensitive) film is used as the image acquiring part. In recent years, use is made of a digital image panel that acquires an X-ray image using a plurality of photosensitive sensors.

In case the X-ray image is acquired by use of the X-ray film, there is a need to replace the X-ray film with a new one each time when the X-ray image is taken. A great deal of time and effort is required in developing the X-ray film. Furthermore, a large storage space is needed to store and manage the image-taking X-ray film and a special environment should be provided to safely store the X-ray film. This poses problems in that it is difficult and costly to provide the large storage space and the special environment.

In an effort to remove the problems inherent in the X-ray film, a digital image panel has become available. The digital image panel enjoys advantages in that it can be used semi-permanently and further that the X-ray image of an object can be confirmed immediately upon the X-ray scanning. Owing to the rapid progress of memory technology and database-related technology, it is possible to readily store a large number of X-ray images in a small-size memory space and also to conduct a search at an increased speed.

FIG. 1 is a view illustrating a conventional X-ray scanning system that makes use of a prior art digital image panel. Referring to FIG. 1, the X-ray scanning system includes an X-ray irradiation unit 1 for generating and irradiating X-rays, a hand-held switch 3 for inputting a user's command to cause the X-rays to be irradiated on an object 4, a digital image panel 5 for acquiring an X-ray image data of the object 4 by sensing the intensity of the X-rays transmitted through the object 4 and converting the sensed intensity to electric signals, and a management computer 7 for initializing the digital image panel 5 according to a user's command prior to irradiating the X-rays on the object 4 and for displaying, storing and managing the acquired image data.

The X-ray irradiation unit 1 includes an X-ray tube for generating the X-rays and a collimator for enabling a user to confirm an X-ray irradiation region prior to irradiating the X-rays on the object 4. The X-ray tube is provided with a cathode terminal and an anode terminal. When a high voltage is applied to the cathode terminal and the anode terminal, thermal electrons are emitted from the cathode terminal and heavily impinged against the anode terminal, thereby generating the X-rays.

Photosensitive cells that generate electric charges in a quantity proportional to the intensity of the X-rays are arranged in the digital image panel 5 in a matrix pattern. The electric charges generated from the respective photosensitive cells are converted to electrical signals. The electrical signals thus converted are compared with a reference signal and are produced as a digital image data indicative of the X-ray image of the object. The digital image data thus produced is supplied to the management computer 7 which in turn displays or stores the digital image data according to a user's command or by means of an automatic execution program pre-stored by a user.

With the X-ray scanning system that makes use of the prior art digital image panel, the user or operator of the system needs to synchronize the preheating state of the X-ray irradiation unit and the initial state of the digital image panel with each other each time when a new X-ray image of the object is taken. In other words, it is necessary for the system user to heat the X-ray irradiation unit 1 and bring the same into an initialized state in which the X-rays can be irradiated at once. Simultaneously, the digital image panel needs to be brought into an initialized state. In order to initialize the digital image panel 5, it is necessary for the user to: first store the image data previously acquired through the digital image panel 5 in the management computer 7; secondly bring the electric charges existing in the photosensitive cells of the digital image panel 5 into a reference state; and thirdly bring the digital image panel 5 into a standby state in which the digital image panel 5 can sense the X-rays transmitted through the object.

Once the task of preheating the X-ray irradiation unit 1 and the task of initializing the digital image panel are all completed in this manner, the user inputs a user's command through the hand-held switch 3 to ensure that the X-rays are irradiated on the object. Then, the X-ray irradiation unit 1 irradiates the X-rays toward the object.

In the prior art X-ray scanning system set forth above, the user or operator needs to have the management computer 7 synchronize the initial state of the digital image panel 5 with the preheating state of the X-ray irradiation unit 1 each time when a new X-ray image of the object is taken. The user or operator also needs to confirm the completion of synchronization through the management computer 7. This causes inconvenience to the user or operator.

DISCLOSURE OF INVENTION

Technical Problem

In view of the afore-mentioned problems inherent in the prior art, it is an object of the present invention to provide an X-ray scanning system capable of simultaneously establishing, i.e., synchronizing, the preheating state of an X-ray irradiation unit and the initialized state of a digital image panel according to a user's command inputted through a hand-held switch unit.

Another object of the present invention is to provide an X-ray scanning system capable of synchronizing the preheating state of an X-ray irradiation unit and the initialized state of a digital image panel using a synchronization command signal and a synchronization completion signal sent and received on a wireless basis.

Technical Solution

In accordance with one aspect of the present invention, there is provided an X-ray scanning system comprising:
an X-ray irradiation unit for generating X-rays and irradiating the X-rays on an object;
a digital image panel for acquiring an X-ray image data of the object by sensing an intensity of the X-rays transmitted through the object and converting the intensity of the X-rays to electrical signals;
a management computer for managing the digital image panel;
a switch unit for sequentially inputting a first user's command and a second user's command to the X-ray irradiation unit;
a synchronization unit for generating a first control signal for initialization of the X-ray irradiation unit and sending the first control signal to the X-ray irradiation unit, when the first user's command is inputted from the switch unit, and for generating and sending a synchronization command signal, when the second user's command is inputted from the switch unit; and
a control unit for initializing the digital image panel in response to the synchronization command signal and then generating and sending a synchronization completion signal,
wherein the synchronization unit is designed to generate a second control signal for causing the X-ray irradiation unit to irradiate the X-rays, when the synchronization completion signal is received from the control unit.

Advantageous Effects

With the present X-ray scanning system mentioned above, it is possible to synchronize the preheating of an X-ray irradiation unit and the initialization of a digital image panel according to a user's command inputted through a hand-held switch unit. It is also possible to synchronize the preheating of an X-ray irradiation unit and the initialization of a digital image panel using a synchronization command signal and a synchronization completion signal sent and received on a wireless basis.

BRIEF DESCRIPTION OF THE DRAWINGS

FIG. 1 is a view illustrating a conventional X-ray scanning system making the digital image panel in accordance with the conventional art.

FIG. 2 is a view schematically showing an X-ray scanning system in accordance with one embodiment of the present invention.

FIG. 3 is a view concretely illustrating one example of a synchronization unit employed in the present X-ray scanning system.

FIG. 4 is a view concretely illustrating one example of a control unit employed in the present X-ray scanning system.

FIG. 5 is a view showing an example of the synchronization unit and the control unit employed in another embodiment of the present X-ray scanning system.

BEST MODE FOR CARRYING OUT THE INVENTION

An X-ray scanning system in accordance with preferred embodiments of the present invention will now be described in detail with reference to the accompanying drawings. FIG. 2 is a view schematically showing an X-ray scanning system in accordance with one embodiment of the present invention.

Referring to FIG. 2, the X-ray scanning system of the present invention includes an X-ray irradiation unit 12 for generating X-rays and irradiating the X-rays toward an object 14 spaced apart a specified distance. The X-ray scanning system further includes a digital image panel 15 for acquiring an X-ray image data of the object 14 by sensing the intensity of the X-rays transmitted through the object 14 and converting the intensity of the X-rays to electric signals. The X-ray scanning system further includes a management computer 19 for controlling the operation of the digital image panel 15, converting the X-ray image data of the object 14 acquired through the digital image panel 15 to a data format selected by a user, displaying the converted image data and storing the converted image data.

The X-ray scanning system further includes a hand-held switch unit 10 for use in inputting user's commands. The X-ray scanning system further includes a synchronization unit 11 for preheating the X-ray irradiation unit 12 according to the user's command inputted through the hand-held switch unit 10 and for generating and sending a synchronization command signal by which the initialization of the digital image panel 15 is synchronized with the operation of the X-ray irradiation unit 12. The X-ray scanning system further includes a control unit 17 for generating a signal for initialization of the digital image panel 15 in response to the synchronization command signal supplied from the synchronization unit 11, sending the initialization signal to the digital image panel 15, and supplying the synchronization unit 11 with a synchronization completion signal informing that the digital image panel 15 has been initialized and is operable in synchronism with the X-ray irradiation unit 12.

The configuration and operation of the X-ray irradiation unit 12 and the digital image panel 15 employed in the present X-ray scanning system is the same as that of the X-ray irradiation unit 1 and the digital image panel 5 referred to above with reference to FIG. 1. Therefore, no detailed description will be given in that regard.

It is preferred that the hand-held switch unit 10 be a two-stage switch capable of sequentially inputting two or more kinds of user's commands. The user's commands inputted through the hand-held switch unit 10 are transferred to the synchronization unit 11 and the X-ray irradiation unit 12. When the hand-held switch unit 10 is pushed to activate the first stage switch, a first user's command for preheating an X-ray tube of the X-ray irradiation unit 12 in preparation for the x-ray scanning of the object 14 is inputted to the synchronization unit 11. When the hand-held switch unit 10 is pushed to activate the second stage switch, a second user's command for generating X-rays, irradiating the X-rays on the object 14 and scanning the object 14 with the X-rays is inputted to the synchronization unit 11.

Responsive to the first user's command, the synchronization unit 11 sends a command for preheating the X-ray irradiation unit 12 to the X-ray irradiation unit 12, thereby bringing the X-ray irradiation unit 12 into a preheated state, i.e., an initialized state. In keeping with the preheating of the X-ray irradiation unit 12, the digital image panel 15 needs to be initialized also. Then, the X-rays are irradiated in response to the second user's command. Prior to irradiating the X-rays, the synchronization unit 11 generates a synchronization command signal for synchronizing the initialization of the digital image panel 15 with the preheating of the X-ray irradiation unit 12 and sending the synchronization command signal to the control unit 17 kept in a remote position. Responsive to the synchronization command signal, the control unit 17 initializes the digital image panel 15 and supplies the synchronization unit 11 with a synchronization completion signal informing that the digital image panel 15 has been initialized in synchronism with the initialization of the X-ray irradiation unit 12. In response to the synchronization completion signal and the second user's command, the synchronization unit 11 supplies the X-ray irradiation unit 12 with an X-ray irradiation command Then, the X-ray irradiation unit 12 irradiates the X-rays toward the object 14 and the digital image panel 15.

Depending on the application of the present invention, various kinds of user interfaces for inputting user's commands may be used in place of the hand-held switch unit 10, which shall fall within the scope of the present invention. Furthermore, the hand-held switch unit 10 may be integrally manufactured with the synchronization unit 11 or the X-ray irradiation unit 12, which shall fall within the scope of the present invention. In addition, the synchronization unit 11 may be integrally manufactured with the X-ray irradiation unit 12, which shall fall within the scope of the present invention.

FIGS. 3 and 4 are views concretely illustrating one example of the synchronization unit 11 and one example of the control unit 17 employed in the present X-ray scanning system. Referring to FIG. 3, the synchronization unit 11 includes an X-ray generation control part 20, a synchronization command signal generating part 21 and a synchronization signal sending and receiving part 23.

When the user pushes the hand-held switch unit 10 to activate the first stage switch, a first user's command for heating the x-ray tube is inputted to the X-ray generation control part 20. In response, the X-ray generation control part 20 generates a first control signal and sends the same to the X-ray irradiation unit 12. Responsive to the first control signal, the X-ray irradiation unit 12 heats the x-ray tube to maintain an initialized state.

When the hand-held switch unit 10 is pushed to activate the second stage switch, a second user's command for generating the X-rays and irradiating the same on the object 14 is inputted to the synchronization command signal generating part 21. At this moment, the synchronization command signal generating part 21 initializes the digital image panel 15 and generates a synchronization command signal for synchronizing the digital image panel 15 with the X-ray irradiation unit 12. The synchronization command signal thus generated is sent to the remote control unit 17 via the synchronization signal sending and receiving part 23.

Referring to FIG. 4, the control unit 17 includes a control signal sending and receiving part 30, a synchronization control part 31 and a synchronization completion signal generating part 33.

When the control signal sending and receiving part 30 receives the synchronization command signal from the synchronization unit 11, the synchronization control part 31 generates a synchronization control signal for initializing the digital image panel 15 and sends it to the digital image panel 15. The digital image panel 15 is initialized in response to the synchronization control signal. Then, the digital image panel 15 sends an initialization completion signal indicative of the completion of initialization to the synchronization completion signal generating part 33. Responsive to the initialization completion signal, the synchronization completion signal generating part 33 generates a synchronization completion signal informing that the digital image panel 15 has been initialized in response to the synchronization command signal. The synchronization completion signal is sent to the synchronization unit 11 through the control signal sending and receiving part 30.

Referring again to FIG. 3, the synchronization completion signal received through the synchronization signal sending and receiving part 23 is inputted to the X-ray generation control part 20. In response, the X-ray generation control part 20 generates a second control signal and feeds it to the X-ray irradiation unit 12. Responsive to the second control signal, the X-ray irradiation unit 12 generates X-rays and irradiates the same toward the object 14 and the digital image panel 15.

Although the synchronization unit 11 and the control unit 17 are of a significantly complicated structure in the illustrated embodiment, they may be simplified by using an MPU and a CPU equipped with an advanced program. FIG. 5 is a block diagram showing another example of the synchronization unit 11 and the control unit 17 employed in another embodiment of the present X-ray scanning system.

Referring to FIG. 5, the synchronization unit 11 includes a first CPU (or a first MPU) 51 for receiving user's commands from the hand-held switch unit 10, sending a command to the X-ray irradiation unit 12 and collecting status information, and a synchronization signal sending and receiving part 23 for sending and receiving signals to and from the first CPU 51 and for communicating with the control unit 17. The control unit 17 includes a second CPU (or a second MPU) 53 for sending a command to the digital image panel 15 and collecting status information, and a control signal sending and receiving part 30 for sending and receiving signals to and from the second CPU 53 and for communicating with the synchronization unit 11.

When the user pushes the hand-held switch unit 10 to activate the first stage switch, a first user's command is inputted to the first CPU 51. Responsive to the first user's command, the first CPU 51 supplies the X-ray irradiation unit 12 with a first control signal for initializing the X-ray irradiation unit 12. In response, the X-ray irradiation unit 12 performs a preheating task and supplies the first CPU 51 with a preheating completion signal informing that the X-ray irradiation unit 12 has been initialized. When the user pushes the hand-held switch unit 10 to activate the second stage switch, a second user's command is inputted to the first CPU 51. Responsive to the second user's command and depending on the reception of the preheating completion signal, the first CPU 51 generates a synchronization command signal and sends it to the synchronization signal sending and receiving part 23. The synchronization signal sending and receiving part 23 sends the synchronization command signal to the control unit 17 on a wireless basis.

In the control unit 17, the control signal sending and receiving part 30 receives the synchronization command signal and sends it to the second CPU 53. Responsive to the synchronization command signal, the second CPU 53 supplies the digital image panel 15 with an initialization command for initializing the digital image panel 15. In response, the digital image panel 15 is initialized and an initialization completion signal informing that the digital image panel 15 has been initialized is sent back to the second CPU 53. Upon recognizing the initialization of the digital image panel 15, the second CPU 53 generates a synchronization completion signal informing that the initialization of the digital image panel 15 has been performed in synchronism with the preheating (initialization) of the X-ray irradiation unit 12. The synchronization completion signal is sent to the control signal sending and receiving part 30. Then, the control signal sending and receiving part 30 sends the synchronization completion signal to the synchronization unit 11 on a wireless basis.

In the synchronization unit 11, the synchronization signal sending and receiving part 23 receives the synchronization completion signal and sends it to the first CPU 51. Responsive to the synchronization completion signal, the first CPU 51 supplies the X-ray irradiation unit 12 with a second control signal for causing the X-ray irradiation unit 12 to irradiate X-rays. In response to the second control signal, the X-ray irradiation unit 12 generates X-rays and irradiates the same to the object 14 and the digital image panel 15.

In another embodiment of the present invention described just above, even when receiving the second user's command from the hand-held switch unit 10, the first CPU 51 sends the synchronization command signal to the control unit 17 only after the preheating completion signal is issued from the X-ray irradiation unit 12. If necessary, the first CPU 51 may be designed to unconditionally send the synchronization command signal to the control unit 17 in response to the second user's command. The first CPU 51 may be configured to send the second control signal to the X-ray irradiation unit 12 after the preheating completion signal is received from the X-ray irradiation unit 12 and after the initialization completion signal is received from the control unit 17. Moreover, the first CPU 51 is not limited to the configuration set forth above but may possibly be modified depending on the design of the X-ray scanning system, while assuring the convenience and reliability thereof.

In the two embodiments of the present invention described above, the first user's command issuing from the hand-held switch unit 10 is used to trigger the initialization (preheating) of the X-ray irradiation unit 12 and the second user's command is used to trigger the initialization of the digital image panel 15. However, the present invention is not limited thereto. As an alternative example, when the first user's command is inputted from the hand-held switch unit 10, the first control signal may be generated to supply an initialization command to the X-ray irradiation unit 12 and, at the same time, the synchronization command signal may be sent to the digital image panel 15 so that the digital image panel 15 can be initialized. Then, if the second user's command is inputted from the hand-held switch unit 10 in a state that the signals informing the completion of initialization of the X-ray irradiation unit 12 and the digital image panel 15 are all received, the second control signal may be supplied to the X-ray irradiation unit 12 so that the X-rays can be irradiated toward the object 14 and the digital image panel 15.

While the present invention has been described with reference to certain embodiments shown in the drawings, this description is given for the purpose of illustration only. It will be understood by those skilled in the art that various changes and modifications may be made without departing from the scope of the invention defined in the claims.

INDUSTRIAL APPLICABILITY

With the X-ray scanning system of the present invention, the X-ray irradiation unit and the digital image panel are initialized in synchronism with each other using wireless synchronization signals generated according to the user's commands inputted through the hand-held switch unit. This makes it possible to conveniently take an X-ray image of the object. Furthermore, it is possible to rapidly and accurately perform the X-ray scanning in a remote position without having to confirm whether the digital image panel has been initialized in synchronism with the preheating state of the X-ray irradiation unit. Therefore, the present X-ray scanning system can find its application in a variety of industrial fields.

The invention claimed is:

1. An X-ray scanning system, comprising:
    an X-ray irradiation unit for generating an X-ray and irradiating on an object with the X-ray;
    a digital image panel for acquiring X-ray image data of the object by sensing an intensity of the X-ray transmitted through the object and converting the intensity of the X-ray to an electrical signal;
    a management computer for managing the digital image panel;
    a hand-held switch unit for inputting a first user command and a second user command;
    a synchronization unit for preheating the X-ray irradiation unit in response to the first user command inputted from the hand-held switch unit, and generating a synchronization command signal in response to the second user command inputted from the hand-held switch unit; and
    a control unit for synchronizing the X-ray irradiation unit and the digital image panel in response to the synchronization command signal received from the synchronization unit, and then generating and sending a synchronization completion signal to the synchronization unit.

2. The X-ray scanning system as recited in claim 1, wherein the hand-held switch unit comprises a two-stage switch unit including:
    a first stage switch for inputting the first user command to preheat the X-ray irradiation unit; and
    a second stage switch for inputting the second user command to generate the synchronization command signal.

3. The X-ray scanning system as recited in claim 1, wherein
    in response to the first user command, the synchronization unit is configured to send a first control signal for preheating the X-ray irradiation unit to the X-ray irradiation unit,
    in response to the second user command, the synchronization unit is configured to generate the synchronization command signal for initializing the digital image panel, thus synchronizing the X-ray irradiation unit and the digital image panel,
    in response to the synchronization command signal from the synchronization unit, the control unit is configured to initialize the digital image panel,
    upon completion of an initialization of the digital image panel, the control unit is configured to generate the synchronization completion signal,
    in response to the synchronization completion signal from the control unit, the synchronization unit is configured to send a second control signal for irradiating the object with the X-ray to the X-ray irradiation unit, and
    in response to the second control signal from the synchronization unit, the X-ray irradiation unit is configured to generate the X-ray and irradiate the object with the X-ray.

4. The X-ray scanning system as recited in claim 1, wherein the synchronization unit includes a first wireless communicating unit for sending the synchronization command signal to the control unit and receiving the synchronization completion signal from the control unit via wireless communication, and
    the control unit includes a second wireless communicating unit for receiving the synchronization command signal from the synchronization unit and sending the synchronization completion signal to the synchronization unit via the wireless communication.

* * * * *